`US008594940B2`

(12) United States Patent
Kano et al.

(10) Patent No.: US 8,594,940 B2
(45) Date of Patent: Nov. 26, 2013

(54) SYSTEM AND METHOD FOR ANALYZING CHROMOSOMAL STATES BASED ON GENE EXPRESSION

(75) Inventors: Makoto Kano, Sagamihara (JP); Tetsuo Shibuya, Yamato (JP)

(73) Assignee: International Business Machines Corporation, Armonk, NY (US)

( * ) Notice: Subject to any disclaimer, the term of this patent is extended or adjusted under 35 U.S.C. 154(b) by 690 days.

(21) Appl. No.: 10/983,405

(22) Filed: Nov. 8, 2004

(65) Prior Publication Data

US 2005/0112670 A1    May 26, 2005

(30) Foreign Application Priority Data

Nov. 20, 2003    (JP) .................................. 2003-391457

(51) Int. Cl.
    *G01N 33/48*    (2006.01)
(52) U.S. Cl.
    USPC .......................................................... 702/19
(58) Field of Classification Search
    None
    See application file for complete search history.

(56) References Cited

PUBLICATIONS

Kano et al., Physiol Genomics, Published Jan. 7, 2003, vol. 13, p. 31-46.*
Conroy et al., Laboratory Investigation, 2000, vol. 80, No. 11, p. 1629-1641.*
Klein et al., J. Exp. Med., 2001, vol. 194, No. 11, p. 1625-1638.*
Kulp et al., Integrating Database Homology in a Probabilistic Gene Structure Model, Proc. Pacific Symp. Biocomputing 1997, p. 1-14.*
Furey et al., Human Molecular Genetics, May 2003, vol. 12, No. 9, p. 1037-1044.*
Cohen et al., Nature Genetics, 2000, vol. 26, p. 183-186.*
Pollack et al., Nature Genetics, 1999, vol. 23, p. 41-46.*
Murphy, University of California, Berkeley, 1999, p. 1-12.*
Holmes et al., American Association for Artificial Intelligence, 2000, p. 202-210.*
Pedersen, Algorithms in Computational Biology, Dissertation, 1999, p. 1-220.*
Sarukkai, Computer Networks, 2000, vol. 33, p. 377-386.*
Hastings, Biometrika, 1970, vol. 57, No. 1, p. 97-109.*
Xing et al. (Bioinformatics, 2001, vol. 17, Suppl. 1, p. S306-S315).*
Dana Pe'er, From Gene Expression to Molecular Pathways, Thesis Submitted for the Degree of "Doctor of Philosophy" Submitted to the Senate of the Hebrew University, Nov. 2003, pp. 1-156.
Fuji et al. "A Preliminary Transcriptome Map of Non-Small Cell Lung Cancer," Cancer Research 62, 3340-3346, Jun. 15, 2002.
Kano et al. "Expression Imbalance Map: A New Visualization Method for Detection,of mRNA Expression Imbalance Regions," Physical Genomics 13, 31-46, Jan. 7, 2003.
Durbin, et al. "Biological Sequence Analysis," Cambridge University Press, 1998.

\* cited by examiner

*Primary Examiner* — Pablo S Whaley

(57) ABSTRACT

Analyzes chromosomal states based on amounts of expression of genes. An example apparatus comprising: a unit for storing probability distribution of amounts of expression of genes for each chromosomal state, assuming any of the chromosomal states in which the distributions of amounts of expression are different; a unit for supplying state transition probability indicating probability in which when each of the genes arrayed on the chromosome assumes any one of the chromosomal states, a certain gene array assumes any one of the chromosomal states; an input unit for receiving an expression amount measurement value of the amount of expression for each of the genes on the chromosome; and a unit for detecting a combination of the chromosomal states maximizing a probability among those that can be assumed by the genes on the chromosome, based on the probability distribution and the state transition probability.

10 Claims, 8 Drawing Sheets

LOGALITHMIC VALUE OF RATIO OF EXPESSION AMOUNT (b)

LOGALITHMIC VALUE OF RATIO OF EXPESSION AMOUNT (c)

LOGALITHMIC VALUE OF RATIO OF EXPESSION AMOUNT

SYSTEM AND METHOD FOR ANALYZING CHROMOSOMAL STATES BASED ON GENE EXPRESSION

FIELD OF THE INVENTION

The present invention relates to an analysis apparatus, an analysis method, a program and a recording medium for analyzing a state of a chromosome, an analysis method for analyzing the same, a program used for executing the same, and a recording medium used for the same.

BACKGROUND OF THE INVENTION

Recently, research concerning genes have been earnestly performed. It has been found that deletions and amplifications of chromosomes are significant factors of incidence and progression of disease such as cancer. For example, when a gene responsible for suppressing tumor growth is deleted owing to chromosome deletion, and when oncogene is amplified owing to chromosome amplification, progression of cancer is accelerated. Accordingly, if regions where deletions and amplifications of chromosome occur are properly detected on chromosomes of cells which become ill, such detection will contribute to an elucidation of gene causing disease.

The following documents are considered:

Non-patent document No. 1: Fuji T, Dracheva T. Player A, Chako S, Clifford R, Strauberg L S, Buetow K, Azumi N, Travis W D, Jen J., A preliminary transcription map of non-small cell lung cancer. Cancer Res 62: 3340-3346, 2002.

Non-patent document No. 2: Kano M, Nishimura K, Ishikawa S, Tsutsumi S, Hirota K, Hirose M, Aburatani H., Expression imbalance map: A new visualization method for detection of mRNA expression imbalance regions. Physical Geomics. 2003 Mar. 18; 13(1): 31-46. Epub 2003 Jan. 7.

Non-patent document No. 3: Durbin R, Eddy S, Krogh A, Mitchison G., Biological sequence analysis. Cambridge University Press. 1998.

A technology for detecting a region where deletions and amplifications of chromosome has been heretofore proposed (refer to non-patent document's Nos. 1 and 2). Non-patent document No. 1 proposes a technology for measuring an amount of expression of each gene on chromosome by use of an expression microarray and for displaying measurement result in the form of a graph at positions on the chromosome where the measured genes are arrayed. Furthermore, non-patent document No. 2 proposes the following technology. That is, when abnormal genes more than prescribed, which satisfy predetermined conditions, exist in some regions on chromosome, that regions are determined to be chromosomal aberration. Description of non-patent document No. 3 will be made later.

According to non-patent document No. 1, though an amount of expression of each gene can be grasped in detail, genes arrayed on the amplification region cannot be detected properly sometimes in spite of showing a small amount of expression. Specifically, when genes showing a small amount of expression are included in a region where genes showing a large amount of expression are concentrically arrayed, this region cannot be sometimes detected as a region of chromosome amplification. For this reason, there is fear that that region cannot be detected properly even if genes causing diseases concentrate.

Figure 8:
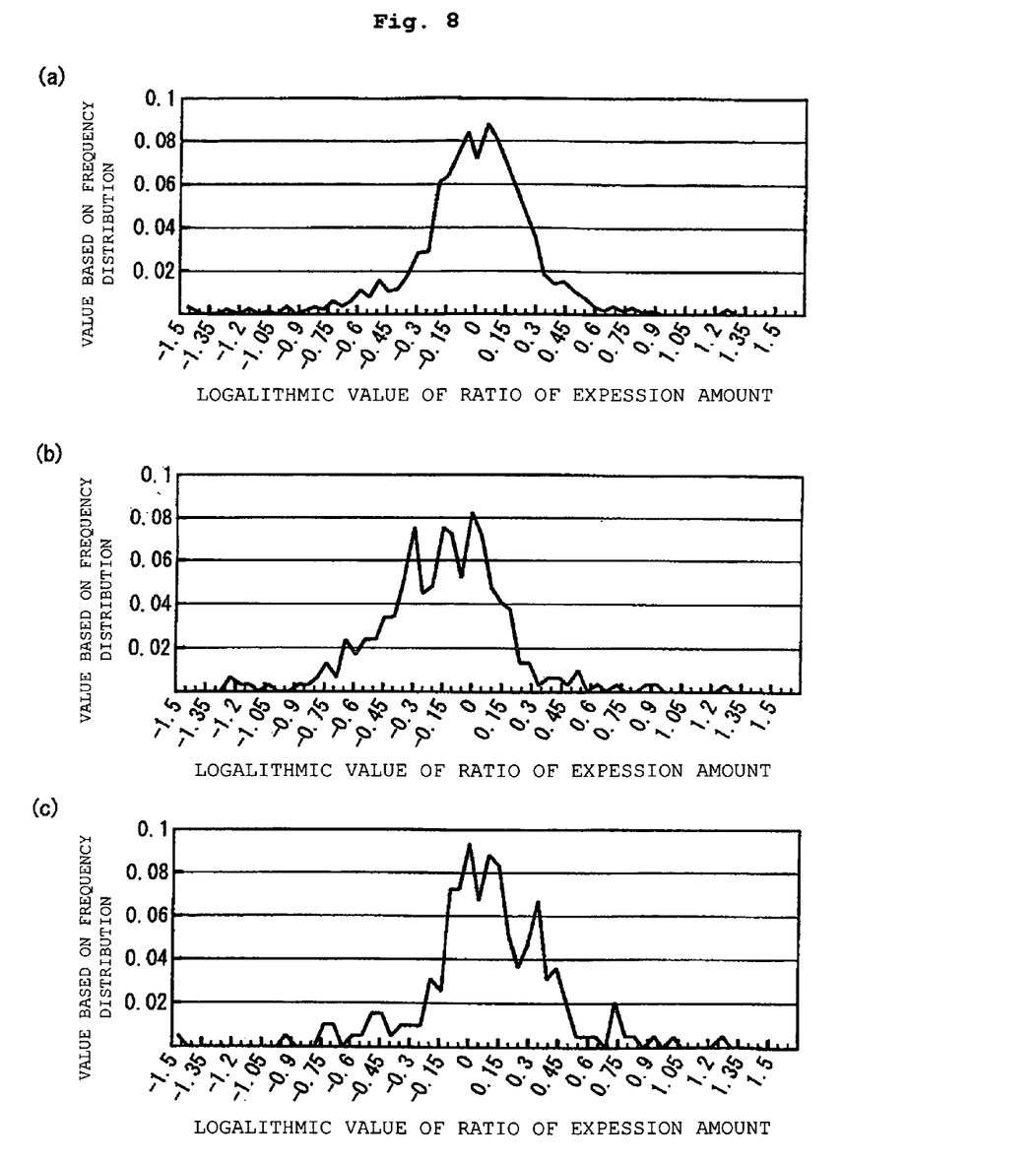
FIG. 8 shows a comparison of cancer cells and normal cells.

As an example, a comparison of cancer cells and normal cells is shown in FIGS. 8(a), 8(b) and 8(c). The transverses in FIGS. 8(a), 8(b) and 8(c) indicate a logarithmic value of a ratio of an amount expression of genes in cancer cells relative to that of genes in normal cells, that is, Fold Change. The vertical axes in FIGS. 8(a), 8(b) and 8(c) indicates a value obtained by normalizing the number of the measured genes so that a measurement result of each gene can be treated evenly. FIG. 8(a) shows a frequency distribution of each gene arrayed on a region where chromosomes of cancer cells are normal. FIG. 8(b) shows a frequency distribution of each gene arrayed on a deletion region of the chromosomes of the cancer cells. FIG. 8(c) shows a frequency distribution of each gene arrayed on an amplification region of the chromosomes of the cancer cells.

As shown in FIGS. 8(a), 8(b) and 8(c), as a whole, the amounts of expression of genes in the amplification region are large, and the amounts of expression in the deletion region tend to be small. However, an attention is paid to one gene, an amount of expression is larger in some cases in the case where this gene is arrayed on the deletion region compared to the case where this gene is arrayed on the amplification region.

Although the technology of non-patent document No. 2 is capable of determining the abnormality of the chromosomes for each of predetermined regions, the abnormal regions cannot be detected precisely sometimes because positions on which genes are arrayed are not considered. To be concrete, in this technology, only the number of each gene in a certain region is an objective to be analyzed, and each gene in this region is treated equivalently, so that influences by a certain gene on other genes depending on distances between them are not considered. Therefore, analysis results may be incorrect.

SUMMARY OF THE INVENTION

An aspect of the present invention is to provide an analysis apparatus and an analysis method, which are capable of solving the foregoing subjects, a program for executing the same, and a recording medium used in the same. This is achieved by combining features defined in the claims. Independent claims define more advantageous embodiments of the present invention.

An example embodiment of the present invention, is an analysis apparatus which analyzes chromosomal states based on amounts of expression of genes. The analysis apparatus comprises: a probability distribution storage unit for storing a probability distribution of amounts of expression of genes for each of a plurality of chromosomal states, each gene arrayed on the chromosome assuming the amount of expression in which the amount of expression is different from others; a state transition probability supply unit for supplying a state transition probability indicating a probability in which when each gene arrayed on the chromosome assumes any one of the chromosomal states, a certain gene arrayed next to each genes assumes any one of the chromosomal states; an expression amount input unit for receiving an expression amount measurement value that is a measurement value of the amount of expression for each gene on the chromosome; and a state detection unit for detecting a combination of the chromosomal states maximizing a probability among those that can be assumed by the plurality of genes on the chromosome, based on the probability distribution and the sate transition probability.

The present invention also provides an analysis method for analyzing the state of the chromosome by use of the analysis apparatus, a program for operating the analysis apparatus, and a recording medium used for the analysis apparatus.

BRIEF DESCRIPTION OF THE DRAWINGS

For a more complete understanding of the present invention and the advantages thereof, reference is now made to the following description taken in conjunction with the accompanying drawings.

DETAILED DESCRIPTION OF THE INVENTION

The present invention provides analysis apparatus and analysis methods capable of solving the foregoing aspects, a program for executing the same, and a recording medium used in the same. In an example embodiment of the present invention, an analysis apparatus which analyzes chromosomal states is based on amounts of expression of genes. An analysis apparatus comprises: a probability distribution storage unit for storing a probability distribution of amounts of expression of genes for each of a plurality of chromosomal states, each gene arrayed on the chromosome assuming the amount of expression in which the amount of expression is different from others; a state transition probability supply unit for supplying a state transition probability indicating a probability in which when each gene arrayed on the chromosome assumes any one of the chromosomal states, a certain gene arrayed next to each genes assumes any one of the chromosomal states; an expression amount input unit for receiving an expression amount measurement value that is a measurement value of the amount of expression for each gene on the chromosome; and a state detection unit for detecting a combination of the chromosomal states maximizing a-probability among those that can be assumed by the plurality of genes on the chromosome, based on the probability distribution and the sate transition probability.

The present invention also provides an analysis method for analyzing the state of the chromosome by use of the analysis apparatus, a program for operating the analysis apparatus, and a recording medium used for the analysis apparatus.

The present invention will be described through advantageous embodiments below. The embodiments described below do not limit the scope of the present invention defined in the claims. All of the combinations of features described in the embodiments are not necessarily essential to solving means of the present invention.

Figure 1:
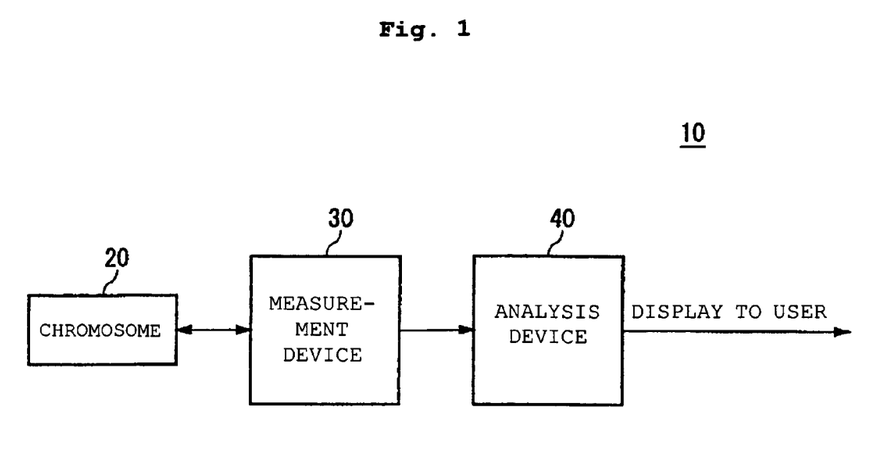
FIG. 1 shows an outline of a chromosome analysis system 10.

FIG. 1 shows an outline of a chromosome analysis system 10. The chromosome analysis system 10 comprises a measurement device 30 and an analysis device 40, and purposes to analyze a state of chromosome 20 based on a measurement value of an amount of expression of each gene included in the chromosome 20. The measurement device 20 measures the amount of expression of each gene included in the chromosome 20 by use of, for example, an expression microarray technology, and sends the measurement results to the analysis device 40. Based on the measurement value of the amount of expression received from the measurement device 30, the analysis device 40 detects a certain combination among those which the genes on the chromosome 20 can take. This combination is the one maximizing a probability in which the amount of expression of each gene coincides with the measurement value of the amount of expression. The analysis device 40 displays the combination to users. It is noted that FIG. 1 is an example, and the analysis device 40 may acquire a measurement value of an expression amount from other server device via a network in stead of the way disclosed in FIG. 1.

Figure 2:
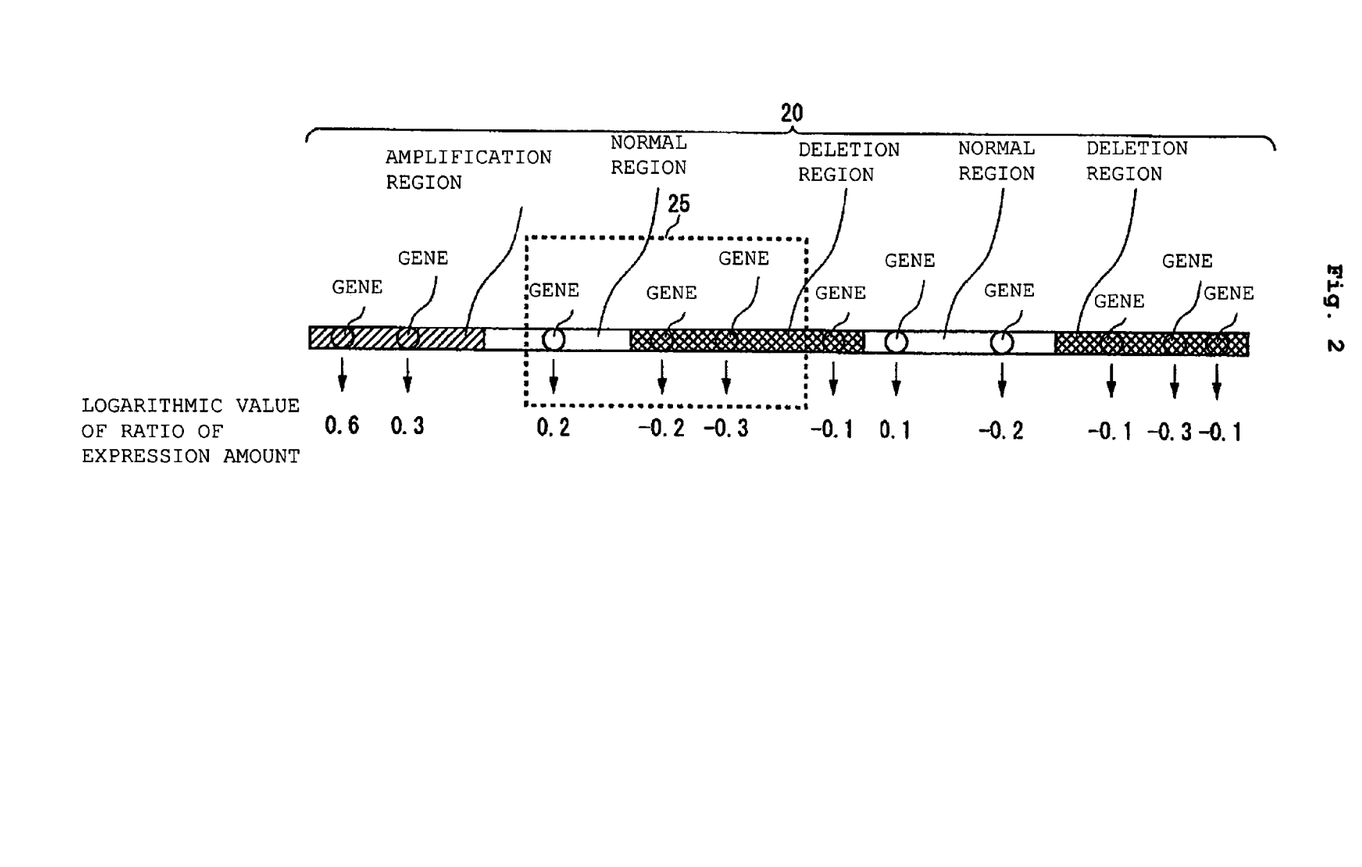
FIG. 2 shows a structure of a chromosome 20 schematically.

FIG. 2 schematically shows a structure of the chromosome 20. A plurality of genes are arrayed on the chromosome 20. Intervals between the genes arrayed on the chromosome 20 are different. Furthermore, it has a an amplification region (shown by slanted lines) where genes, which are essentially single, are duplicated; a deletion region (shown by double slanted lines) where genes to be essentially arrayed are deficient; and a normal region which is neither the amplification region nor the deletion region.

FIG. 2 shows "Fold Change" for each gene on the chromosome of a cancer cell. "Fold Change" of the amounts expression of the genes in the amplification region is larger than zero in many cases. "Fold Change" of the amounts of expression of the genes in the deletion region is smaller than zero in many cases.

FIGS. 3(a) and 3(b) shows parameters of the chromosome 20 which the analysis device 40 uses for analysis. In these drawings, the region 25 of the chromosome 20 shown in FIG. 2 will be described as an example. As shown in FIG. 3(a), when the chromosome 20 is observed sequentially from an end thereof the genes arrayed on (k−1) position, k-th position and (k+1) position are a gene $g_{k-1}$, a gene $g_k$ and a gene $g_{k+1}$. Specifically, the genes $g_{k-1}$ and $g_k$ are arrayed on positions next to each other, and the genes $g_k$ and $g_{k+1}$ are arrayed on positions next to each other. The fact that the genes are arrayed on positions next to each other implies that other genes are not arrayed between these genes. Alternatively, this fact implies that there are no portions elucidated as those where a gene exists between other genes.

The distance between the gene $g_{k-1}$ and the gene $g_k$ is $L_k$ times a unit distance previously determined, for example, a distance between bases. Furthermore, the distance between the gene $g_k$ and the gene $g_{k+1}$ is $L_{k+1}$ the unit distance. Specifically, as shown in FIG. 3(b), each gene is practically next to a corresponding base. For example, the gene $g_{k-1}$ is next to the base 300. A plurality of bases are arrayed between the genes, and the number obtained by multiplying the unit distance with the number of the bases shall be the distance between the genes. Alternatively, the unit distance is a length of the base, and the distance between the genes may be a length obtained by multiplying the number of the bases with the length of the base.

It is noted that a gene is a group of a plurality of bases. Accordingly, the gene itself has a predetermined length. However, because the distance between the genes is fully longer than that of the gene, it is thought that the length of the gene itself has a small effect on analysis. Therefore, in this embodiment, the length of the gene is expediently regarded to be a length of one base.

Figure 3:
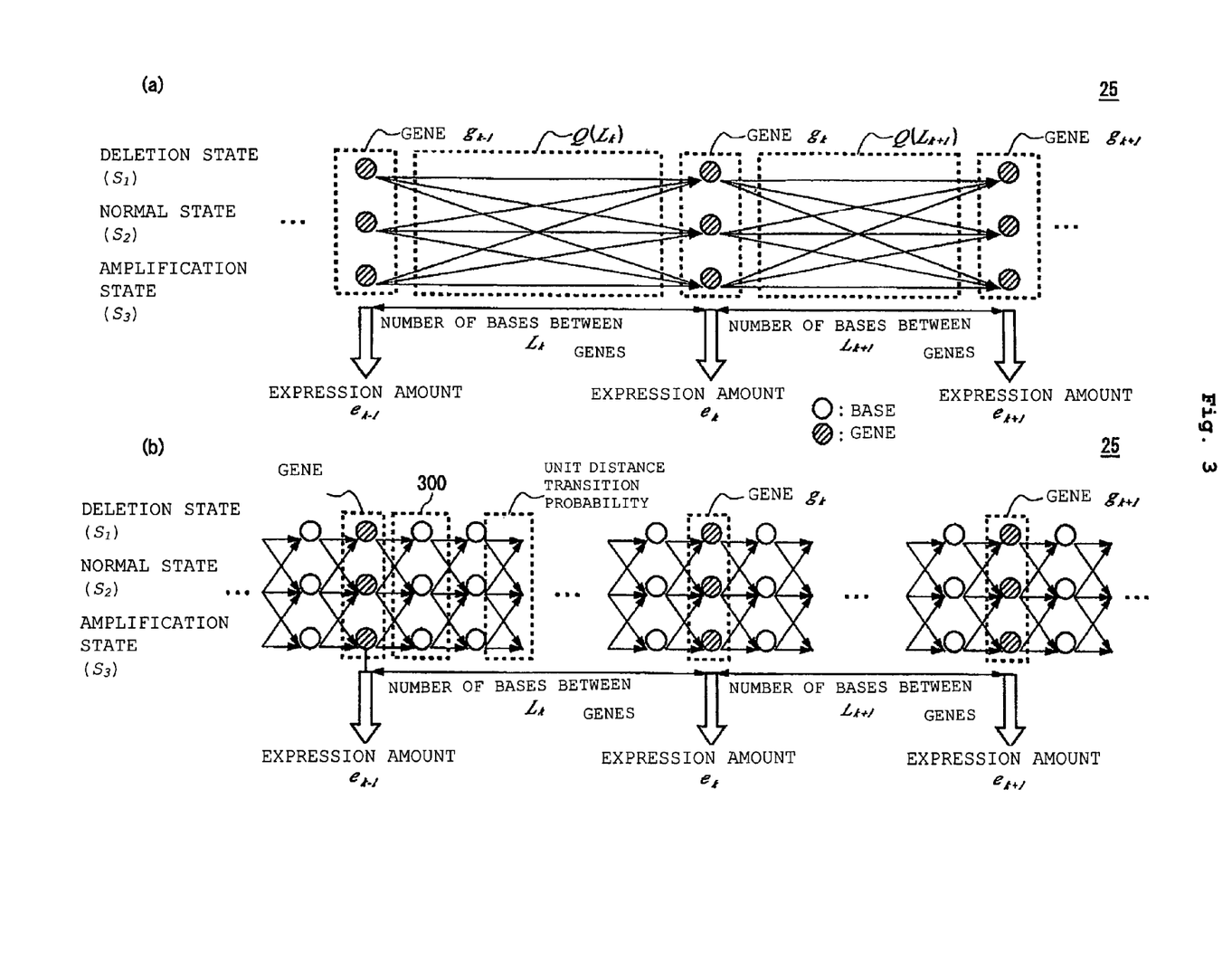
FIG. 3 shows parameters of the chromosome 20 which an analysis apparatus 40 uses for analysis.

The amounts of expression of the gene $g_{k-1}$, $g_k$ and $g_{k+1}$ measured by the measurement device 30 are amounts of expression $e_{k-1}$, $e_k$, and $e_{k+1}$, respectively. Here, an amount of expression of each gene may be a measurement value of an amount of protein produced from each gene, and may be a measurement value of an amount of m-RNA produced from each gene.

Each gene on the chromosome 20 assumes any of chromosomal states in which amounts of expression are different from each other. For example, a chromosomal state of each gene is any of a deletion state ($S_1$), an amplification state ($S_3$) and a normal state ($S_2$). The deletion state ($S_1$) indicates that the gene exists in a deletion region of the chromosome, the amplification state ($S_3$) indicates that the gene exists in an amplification region thereof, and the normal state ($S_2$) indicates that the gene exist in a normal region thereof. The difference of the amounts of expression includes not only the case where the amounts of expression are practically different, but also the case where probability distributions of the amounts of expression are different. For example, the probability distribution of the amount of expression of the gene is different depending on in which state among the deletion, amplification and normal states the gene assumes.

Alternatively, the chromosomal state may be a state of a promoter that is a group of bases controlling the action of each gene. To be concrete, the chromosomal state of each gene may be a state in which the promoter of the gene activates the action of the gene, or may be a state in which the promoter of the gene suppresses the action of the gene. Specifically, when the promoter of the gene is in a state where it activates the action of the gene, the amount of expression of the gene increases. When the promoter of the gene is in a state where it suppresses the action of the gene, the amount of expression of the gene decreases. As described above, the chromosomal state may be not only a state based on a genome-level mutation including deletion and amplification of chromosome, but also a sate based on a control-level mutation controlling the amount of expression.

Furthermore, each of the bases between the genes is arrayed on any of the deletion region, the normal region and the amplification region. The base in the deletion region is called a deletion state, the base in the normal region is called a normal state, and the base in the amplification region is called an amplification state.

For each of the genes on the chromosome, the arrows of FIG. 3(a) indicate a state transition in which when a certain gene assumes any of chromosomal states, genes arrayed next to this certain gene assume any of the chromosomal states respectively. A state transition probability that is a probability of this state transition, for example, $Q(L_k)$ and $Q(L_{k+1})$, is determined for each arrow. For each of the genes and the bases, the arrows of FIG. 3(b) indicate a state transition in which when a certain gene or a certain base assumes any of the chromosomal states, genes or bases arrayed next to this certain gene or base assumes any of the chromosomal states respectively. A unit distance transition probability that is a probability of this state transition is determined for each arrow.

Figure 4:
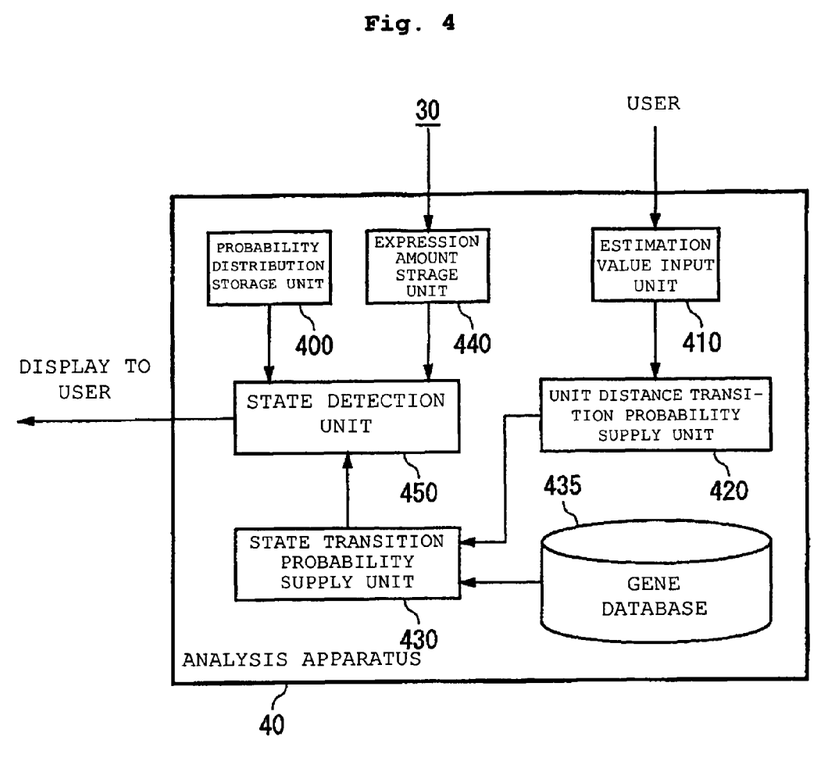
FIG. 4 shows a function block diagram of the analysis apparatus 40.

FIG. 4 shows a function block diagram of the analysis device 40. The analysis device 40 comprises a probability distribution storage unit 400, an estimation value input unit 410, a unit distance transition probability supply unit 420, a state transition probability supply unit 430, an expression amount input unit 440, and a state detection unit 450. The probability distribution storage unit 400 stores a probability distribution of an amount of expression of a gene when the gene assumes any of the deletion, amplification and normal states. For example, when the chromosome 20 is sequentially observed from an end thereof, the probability distribution storage unit 400 stores $b_i(e_k)$ determined by the following equation (4) as a probability distribution of an amount of expression when a gene arrayed at the kth position assumes Si, that is, as a probability that the amount of expression is from $e_k$ to $e_k+\Delta e$. It is noted that $\mu_i$ is a mean value of the amount of expression, and $\sigma_i$ a variance value of the amount of expression. Here, the mean and variance values of the amount of expression may be values measured previously by other experiments.

$$b_i(e_k) = \frac{1}{\sqrt{2\pi\sigma_i}} \exp\left(-\frac{(e_k - \mu_i)^2}{2\sigma_i^2}\right) \times \Delta e \quad (4)$$

Alternatively, the probability distribution storage unit 400 may store a probability distribution in which a probability does not change successively, for example, a probability in which an amount of expression is previously determined based on a chromosomal state alone. The probability distribution may a frequency distribution itself of the amount of expression measured by other experiments.

From the user, the estimation value input unit 410 receives an estimation value of a deletion distance that is a length of the continuous deletion region in the chromosome 20, as well as an estimation value of an amplification distance that is a length of the continuous amplification region in the chromosome 20. Furthermore, from the user, the estimation value input unit 410 receives an estimation value of a region ratio that is a ratio of the deletion, amplification and normal regions. Based on the deletion distance, the amplification distance and the region ratio, which are inputted by the estimation value input unit 410, the unit distance transition probability supply unit 420 generates a unit distance transition probability that is a state transition probability between two genes when these two genes are arrayed on the chromosome 20, which are next to each other at an interval of a unit distance previously determined. The unit distance transition probability supply unit 420 supplies the unit distance transition probability to the state transition probability supply unit 430.

Based on, for example, a vector indicating a probability in which a predetermined position of the chromosome 20 becomes any of the deletion, amplification and normal regions, the unit distance transition probability supply unit 420 supplies as a unit distance transition probability a matrix Q for calculating a vector indicating a probability in which a position distant from the predetermined position by the unit distance becomes any of the deletion, amplification and normal regions. The matrix Q is expressed by the following equation (5), for example.

$$Q = \{q_{ij}\} = \begin{pmatrix} 1-\alpha & \alpha & 0 \\ \beta_1 & 1-\beta_1-\beta_2 & \beta_2 \\ 0 & \gamma & 1-\gamma \end{pmatrix} \quad (5)$$

In the equation (5), when the chromosome 20 is sequentially observed from an end thereof, a probability in which a position distant from a position, which is the deletion region, by the unit distance becomes the normal region is $\gamma$, and a probability in which a position distant from a position, which is the normal region, by the unit distance becomes the deletion region is $\beta_1$. A probability in which a position distant from a position, which is the normal region, by the unit distance becomes the amplification region is $\beta_2$, and a probability in which a position distant from a position, which is the amplification region, by the unit distance becomes the normal region is γ. Furthermore, γ, $β_1$, $β_2$ and γ range from zero to one, and the matrix Q is a regular matrix.

The transition probability supply unit 430 receives the unit distance transition probability from the state transition probability supply unit 430, and acquires the distance between the two genes arrayed next to each other on the chromosome from a gene database 435. For example, the distance between the genes is predetermined according to a sort of species having chromosomes, and the distance between the genes is beforehand stored in the gene database 435. Alternatively, the state transition probability supply unit 430 may allow other measurement devices to measure the distance between the genes, and may acquire data indicating the distance between the genes from other measurement devices.

For each of genes on the chromosome 20, the state transition probability supply unit 430 generates a state transition probability indicating a probability in which when a certain gene assumes any of chromosomal states, a gene arrayed next to this certain gene assumes any of the chromosomal states, and stores the state transition probability in the state detection unit 450. To be concrete, the state transition probability supply unit 430 generates the state transition probability between the two genes arrayed next to each other on the chromosome by multiplying the unit distance transition probability with each other by the number of times in accordance with the acquired distance between the genes.

More specifically, the state transition probability supply unit 430 generates a product of an inverse matrix of a matrix W, an L-power of a matrix Λ, and the matrix W. The matrix W is obtained by arranging each eigenvector of the matrix Q in the row direction, and the matrix Λ is obtained by arranging each eigenvalue of the matrix Q in diagonal elements. The matrix W, the L power of the matrix Λ, and Q(L) are expressed by the following equation (6).

$$W = \begin{pmatrix} w_1 \\ w_2 \\ w_3 \end{pmatrix}, \quad (6)$$

$$\Lambda^L = \begin{pmatrix} 1 & 0 & 0 \\ 0 & \lambda_2^L & 0 \\ 0 & 0 & \lambda_3^L \end{pmatrix},$$

$$Q(L) = \{q_{ij}(L)\} = Q^L = W^{-1}\Lambda^L W$$

Thus, in the state transition probability which the state transition probability supply unit 430 supplies, a probability, in which the chromosomal states of the aforementioned genes adjacent to each other are equal, becomes higher when a distance between them is shorter than when the distance between them is longer.

For each of the genes on the chromosome 20, the expression amount input unit 440 receives from the measurement device 30 an expression amount measurement value that is a measurement value of the amount of expression. Based on the probability distribution stored in the probability storage unit 400 and the state transition probability acquired from the state transition supply unit 430, the state detection unit 450 detects a combination of the chromosomal states maximizing a probability among those that can be assumed by the plurality of genes on the chromosome 20. In this detected combination, the amounts of expression of the plurality of genes are the expression amount measurement value.

For example, the state detection unit 450 sets up a Hidden Markov Model in which the plurality of genes states are a hidden state group, the amounts of expression of the plurality indicated by the expression amount measurement value are an output sequence, and the probability distribution is an output probability in each of the chromosomal state. The state detection unit 450 calculates a state transition sequence maximizing the hidden-state state transition probability in the Hidden Markov Model. Thus, the state detection unit 450 detects the combination maximizing the probability, in which the amounts of expression of the plurality of genes are the expression amount measurement value. Then, the state detection unit 450 further detects an abnormal region of the gene based on the detection result to display it to the user.

To be concrete, the deletion state $S_1$, the normal state $S_2$, and the amplification state $S_3$ are made to be a hidden state in the Hidden Markov Model. When the chromosome 20 is sequentially observed from an end thereof, the equation (7) which expresses a group of the amount of expression from the gene arrayed on the m-th position to the gene arrayed on the n-th position is made to be the output sequence of the Hidden Markov Model. It is noted that $e_1$ represents the amount of expression of the gene arrayed on the l-th position when the chromosome 20 is observed sequentially from its end. The equation (8) which represents a group of the chromosomal state of the genes ranging arrayed from the m-th position to the n-th position is a state transition sequence to be calculated.

$$E_m^n = \{e_m, e_{m+1}, \ldots, e_l, \ldots, e_{n-1}, e_n\} \quad (7)$$

$$X_m^n = \{X_m, X_{m+1}, \ldots, X_l, \ldots, X_{n-1}, X_n\} \quad (8)$$

Here, by using, for example, a Viterbi algorithm (see non-patent document No. 3), the state detection unit 450 calculates the equation (8) which is a state transition sequence maximizing a probability in which the output sequence represented by the equation (7) is output. The calculation method will be described in detail. First, in the Hidden Markov Model, the output sequence in which the first to k-th genes are previously determined is output, and the highest probability in which the gene arrayed on the k-th position assumes the chromosomal state $s_i$ is expressed by the equation (9). The immediately previous chromosomal state, which gives the highest probability value, is expressed by the equation (10).

$$\delta_k(i) = \max_{x_1^{k-1}} P(X_1^{k-1}, X_k = S_i, E_1^k) \quad (9)$$

$$S_{\phi_k(i)} \quad (10)$$

$$\phi_k(i) \quad (10)'$$

In the following descriptions, the just-before chromosomal state, which gives the highest probability value represented in the equation (9), is represented in the equation (10)' on behalf of the equation (10), for the simplification of the equation (9).

The state detection unit 450 generates the state transition sequence for the genes arrayed on the first to N-th positions when the chromosome 20 is observed from its end by the processing shown in the following steps.

(Step 1)

The state detection unit 450 initializes the highest probability value for the chromosomal states $S_i$ (i=1, 2 and 3) of the genes and the immediately previous chromosomal state which gives the highest probability value (Equation (11)) when it is assumed that a 0-th gene next to the first gene on the chromosome 20 exist. For example, the state detection unit 450 initializes the highest probability value for the chromosomal states $S_i$ (i=1, 2 and 3) by each element of the eigenvector when the eigenvalue of the matrix Q is set to one.

$$\delta_0(i) = \hat{w}_i \quad (11)$$

$$\varphi_0(i) = 0$$

(Step 2)

The state detection unit 450 performs the calculation represented in the equation (12) recursively for the genes $g_k$ (k=1, 2, . . . , and N) and the chromosomal states $s_i$ (i=1, 2 and 3).

$$\delta_k(j) = \max_i \lfloor \delta_{k-1}(i) q_{ij}(l_k) \rfloor b_j(e_k) \quad (12)$$

$$\varphi_k(j) = \arg\max_i \lfloor \delta_{k-1}(i) q_{ij}(l_k) \rfloor$$

(Step 3)

The state detection unit 450 calculates the maximum of the probability value as the equation (13) by the processes of Step 2, and calculates the chromosomal state, which the N-th gene assumes, as the equation (14) when the probability value is given.

$$\hat{P} = \max_i \delta_N(i) \quad (13)$$

$$\hat{X}_N = \arg\max_i \delta_N(i) \quad (14)$$

(Step 4)

The state detection unit 450 generates the state transition sequence by coupling the chromosomal states calculated by the equation (12). To be concrete, the state detection unit 450 executes the equation (15) for k=N−1, . . . , and 1.

$$\hat{X}_k = \varphi_{k+1}(\hat{X}_{k+1}) \quad (15)$$

As described above, the state detection unit 450 sequentially calculates the probability values for the genes arrayed on the chromosome 20 by the calculation shown by the equation (12). The calculation shown in the equation (12) requires a calculation amount in proportion to the number of the chromosomal states. Here, since the number of the chromosomal state is, for example, three of the deletion, normal and amplification states, and the state detection unit 450 can execute the above described calculation with the calculation amount and the memory amount in proportion to the number of the genes. The analysis apparatus 40 shows an extremely high efficiency in comparison with the fact that the technology of non-patent document No. 2 requires the calculation amount and the memory amount in proportion to the square of the number of the genes.

Figure 5:
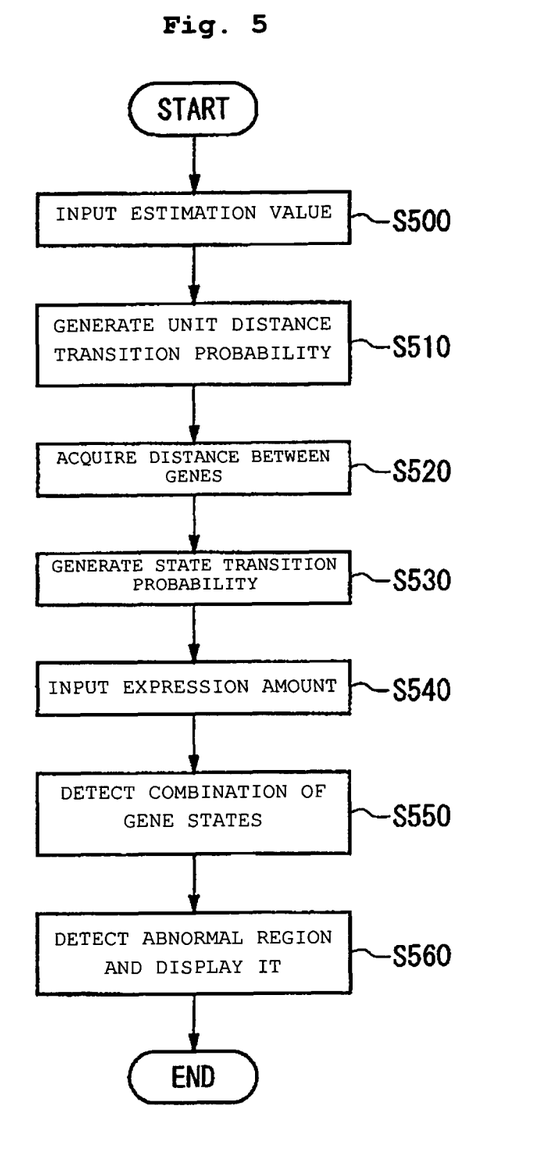
FIG. 5 shows an operation flow in which the analysis apparatus 40 analyses a state of a gene.

FIG. 5 shows an operation flow in which the analysis apparatus 40 analyzes the state of the chromosome. The estimation value input unit 410 receives from the user an estimation value of the deletion distance that is the length of the deletion region continuous in the chromosome 20 and an estimation value of the amplification distance that is the length of the amplification region continuous in the chromosome 20 (S500). Furthermore, the estimation value input unit 410 receives an estimation value of the region ratio that is the ratio of the deletion, amplification and normal regions.

The unit distance transition probability supply unit 420 generates the unit distance transition probability based on the deletion distance, the amplification distance and the region ratio, which are inputted from the estimation value input unit 410 (S510). For example, the unit distance transition probability supply unit 420 generates α and β based on the following characteristic.

The probability in which the deletion region continues for a length equal to that k times the unit distance is a value obtained by raising $(1-\alpha)$ to k-power and multiplying a with $(1-\alpha)^k$. Accordingly, an expected value of the length of the continuous deletion region is expressed by the following equation (16). Here, it is regarded that a is fully smaller than one, and the final transformation of the equation (16) is performed.

$$\text{Distance Between Bases} \times \sum_{k=1}^{\infty} k\alpha(1-\alpha)^k = \quad (16)$$

$$\text{Distance Between Bases} \times \alpha \lim_{n \to \infty} \sum_{n \to}^{n} k(1-\alpha)^k =$$

$$\text{Distance Betweenases} \times \text{etwe Bases} \times$$

$$\alpha \lim_{n \to \infty} \left\{ \frac{1-\alpha}{\alpha^2} - \frac{(1-\alpha)^{n+1}}{\alpha^2} - n(1-\alpha)^{n+1} \right\} =$$

$$\text{Distance Betweenses} \times \text{etwee Bases} \times \frac{1-\alpha}{\alpha} =$$

$$\text{Distance Between Bases} \times \frac{1}{\alpha}$$

When the chromosome 20 is sequentially observed from an end thereof, the unit distance transition probability supply unit 420 generates a probability a in which a position distant from a position of the deletion region by the unit distance becomes the normal region by use of the foregoing characteristic, by multiplying the unit distance with the inverse number of the deletion distance inputted from the estimation value input unit 410. Here, if a of the equation (16) is substituted for γ, the similar characteristic to that of the deletion region is derived for the amplification region. Accordingly, the unit distance transition probability supply unit 420 can generate a probability in which a position distant from a position of the amplification region by the unit distance becomes the normal region by multiplying the unit distance with the inverse number of the amplification distance inputted from the estimation value input unit 410.

Subsequently, the unit distance transition probability supply unit 420 generates $\beta_1$ and $\beta_2$ based on the characteristic of the matrix Q indicating the unit distance transition probability, as shown below.

First, the eigenvalue of the matrix Q is obtained. If the equation (17) that is a characteristic equation of the matrix Q is figured, the equation (18) is obtained as an eigenvalue. Here, since α, $\beta_1$, $\beta_2$ and γ are larger than zero and smaller than one, $\lambda_2$ and $\lambda_3$ are larger than zero and smaller than one.

$$|Q - \lambda I| = (1-\lambda)\{(1-\lambda)^2 - (\alpha+\beta_1+\beta_2+\gamma)(1-\lambda) + (\alpha\beta_2+\beta_1\gamma+\gamma\alpha)\} = 0 \quad (17)$$

$$\lambda = 1, 1 - \left\{ \frac{(\alpha+\beta_1+\beta_2+\gamma) \pm \sqrt{(\alpha-\beta_1+\beta_2-\gamma)^2 + 4\beta_1\beta_2}}{2} \right\} = \quad (18)$$

$$\lambda_1(=1), \lambda_2, \lambda_3$$

A limiting value of the matrix Q(L) represented in the equation (6) in the case where L is infinite is a matrix A of the equation (19). Here, $w_1$ is an eigenvector of the matrix Q in the case where an eigenvalue is one, elements of $w_1$ are $\beta_1\gamma$, $\gamma\alpha$, and $\alpha\beta_2$ as shown in the equation (20).

$$Q(\infty) = \lim_{l \to \infty} Q(l) = \lim_{l \to \infty} Q^l = \begin{pmatrix} w_1 \\ w_1 \\ w_1 \end{pmatrix} = A \quad (19)$$

$$w_1 = (\hat{w}_1, \hat{w}_2, \hat{w}_3) = \frac{1}{\alpha\beta_2 + \beta_1\gamma + \gamma\alpha}(\beta_1\gamma, \gamma\alpha, \alpha\beta_2) \quad (20)$$

As described above, when L is infinite, the probability, in which the position distant from the deletion region by L-times the unit distance is the deletion region, is in proportion to $\beta_1\gamma$, and the probability, in which the position distant from the normal region by L-times the unit distance is the normal region, is in proportion to $\gamma\alpha$. Furthermore, the probability, in which the position distant from the amplification region by L-times the unit distance is the amplification region, is in proportion to $\alpha\beta_1$. Accordingly, the region ratio that is the ratio of the regions on the chromosome is the deletion region: the normal region: the amplification region=$\beta_1\gamma$:$\gamma\alpha$:$\alpha\beta_2$.

By the above described characteristic, the unit distance transition probability supply unit 420 generates $\beta_1$ and $\beta_2$ based on the two equations about $\alpha$, $\beta 1$, $\beta 2$ and $\gamma$, in which the region ratio input by the estimation value input unit 410 is derived from $\beta_1$:$\gamma\alpha$:$\alpha\beta_2$, and based on the already calculated values of $\alpha$ and $\gamma$.

As described in S510, the unit distance transition probability supply unit 420 can generate the unit distance transition probability based on information such as a length for which a predetermined region is continuous on the chromosome and a ratio occupied by the region, which can be grasped by experts such as medical physicians.

Subsequently, the state transition probability supply unit 430 acquires the distance between the two genes arrayed next to each other on the chromosome from the gene database 435 (S520). The state transition probability supply unit 430 generates a state transition probability for each gene on the chromosome (S530). The expression amount input unit 440 receives from the measurement device 30 an expression amount measurement value that is a measurement value of an amount of expression for each gene on the chromosome (S540).

Based on the probability distribution stored in the probability distribution storage unit 400 and the state transition probability acquired from the state transition probability supply unit 430, the state detection unit 450 detects a combination of the chromosomal states maximizing a probability in which the amounts of expression of genes are the expression amount measurement value, among the combinations of the chromosomal states which the genes on the chromosome can assume (S550). The state detection unit 450 further detects an abnormal region of the gene based on the detection result, and displays it to the user (S560).

Figure 6:
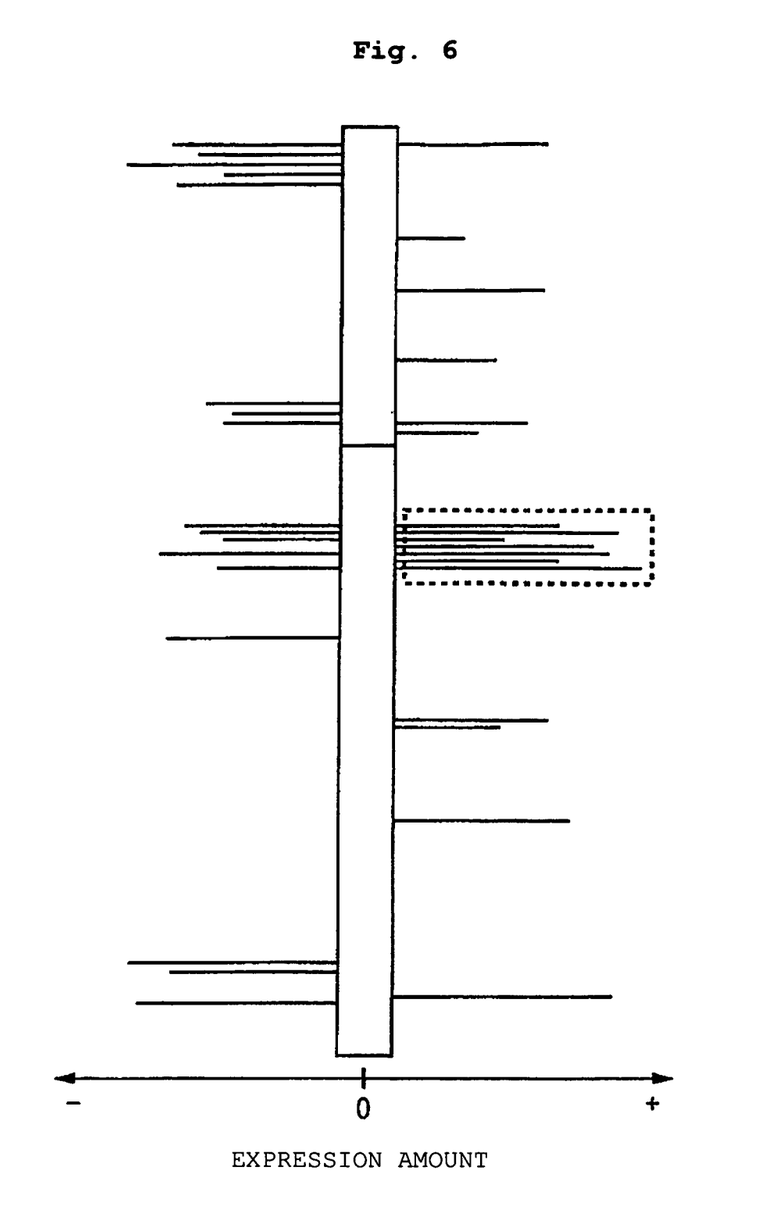
FIG. 6 shows an example of a screen displayed by a state detection unit 450.

FIG. 6 shows an example of a screen displayed by the state detection unit 450. In the drawing, the chromosome 20 is displayed vertically in the center of the screen like a stick. The amount of expression of measured for each gene on the chromosome is displayed as a linear graph on a position where the gene is arrayed on the chromosome 20. Specifically, for example, this linear graph shows the measurement result by an expression microarray. As shown in this drawing, a gene showing a small amount of expression is included sometimes in a region in which an amount of expression is comparatively large. This situation is caused by a function of a feedback control for recovering an abnormal state in an organism. According to conventional arts, since the amount of expression itself is an object to be analyzed, such a region cannot be detected as an abnormal region in some cases.

Contrary to this, based on the combination of the chromosomal states detected by regarding the expression of the gene as the Hidden Markov Model, the state detection unit 450 detects a portion in which a distance between adjacent genes is no more than a previously determined length as an abnormal region on the chromosome 20, among portions in which genes in the amplification state exist continuously or portions in which genes in the deletion state exist continuously. The state detection unit 450 displays the detected portion. Specifically, when the distance between the genes themselves is long to some extent though there are regions where the genes in the amplification state or the deletion state continuously exist, the state detection unit 450 should not detects these regions as a continuous abnormal region. Accordingly, the state detection unit 450 detects these regions as discrete abnormal regions.

In the drawing, to be concrete, the state detection unit 450 displays the detected abnormal region as a rectangular region expressed by dotted lines. As described above, the analysis apparatus 40 can suitably detect even an abnormal region that cannot be detected only by measuring the amount of expression in detail.

Furthermore, according to experiments using four specimens of a cell line of lung cancer, as a result that this embodiment was compared with the technology of non-patent document No. 2, it was confirmed that a recall ratio and precision of the abnormal region detection, and a calculation speed for the abnormal region were more increased. To be concrete, the recall rate and the precision were improved by 11% and 22%, respectively, and a harmonic average of them is improved by 19%. Moreover, it was confirmed that a calculation time required 141.95 seconds in the technology of non-patent document No. 2 was shortened to 6.8 seconds, and processing was made to be about 21 times higher.

Figure 7:
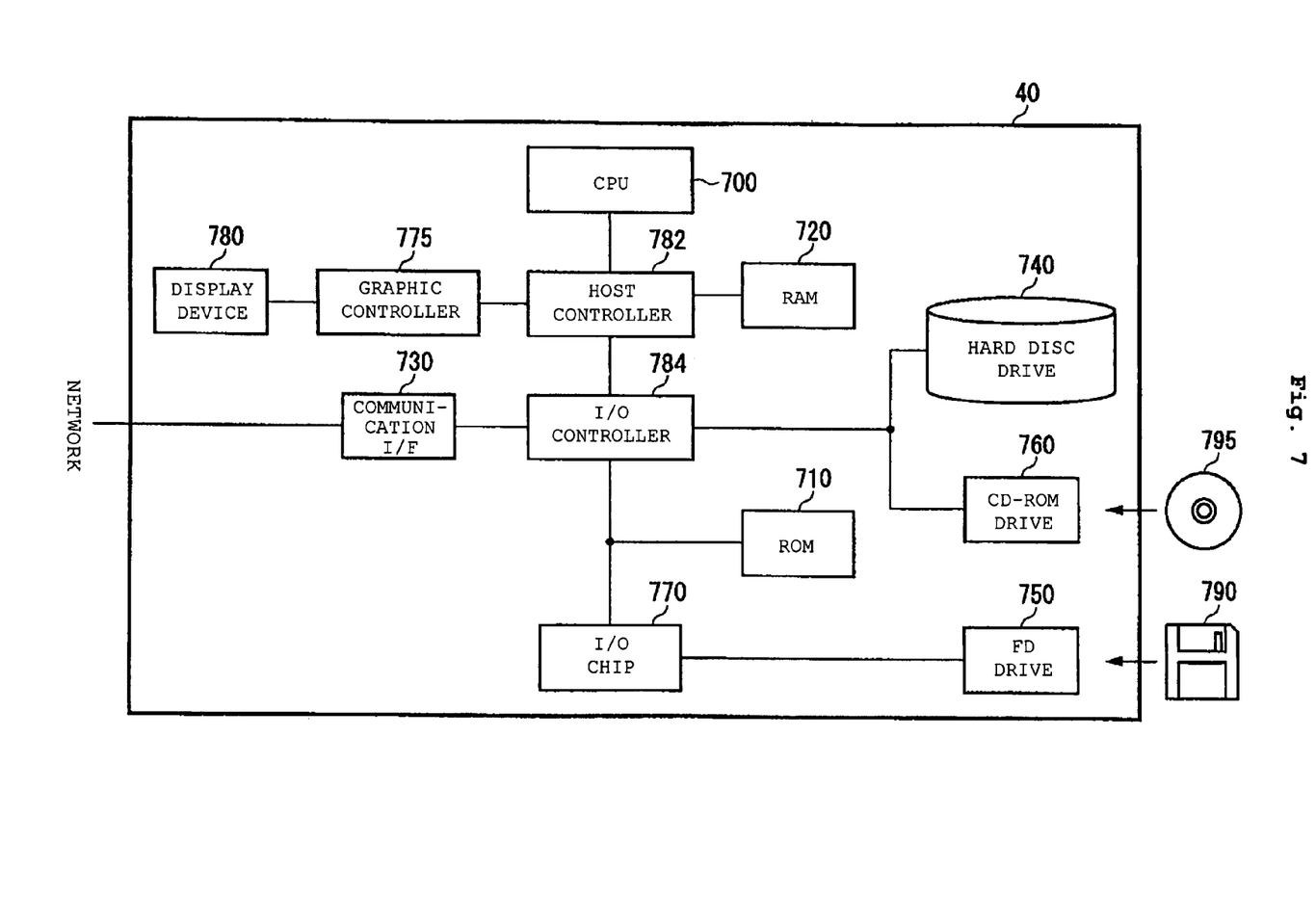
FIG. 7 shows an example of a hardware structure of the analysis apparatus 40.

FIG. 7 shows an example of a hardware structure of the analysis apparatus 40. The analysis apparatus 40 comprises a CPU peripheral section having a CPU 700, a RAM 720, a graphic controller 775 and a display device 780, which are mutually coupled to each other by a host controller 782; an I/O section having a communication interface 730 coupled to the host controller 782 by an I/O controller 784, a hard disc drive 740, and a CD-ROM drive 760; and a legacy I/O section having a ROM 710 coupled to the I/O controller 784, a flexible disc drive 750 and an I/O chip 770.

The host controller 782 couples the RAM 720, the CPU 700 which accesses the RAM 720 at a high transfer rate, and the graphic controller 775. The CPU 700 operates based on a program stored in the ROM 710 and the RAM 720, and controls the above described sections. The graphic controller 775 acquires image data which the CPU 700 and the like generate on a frame buffer provided in the RAM 720, and allows the image data to display on the display device 780. Alternatively, the graphic controller 775 may include a frame buffer therein, which stores the image data which the CPU 700 and the like generate.

The I/O controller 784 couples the host controller 782, the communication interface 730 which is a comparatively high-speed I/O device, the hard disc drive 740, and the CD-ROM drive 760. The communication interface 730 communicates with an external device via a network. The hard disc drive 740 stores a program and data which the analysis apparatus 40 uses. The CD-ROM drive 760 reads out the program or the data from the CD-ROM 795, and supplies it to the I/O chip 770 via the RAM 720.

The comparatively low-speed I/O devices such as the ROM 710, the flexible disc drive 750 and the I/O chip 770 are coupled to the I/O controller 784. The ROM 710 stores a boot program which the CPU 700 executes during the start-up process of the analysis apparatus 40, and a program depending on hardware of the analysis apparatus 40. The flexible disc drive 750 reads out the program or the data from the flexible disc drive 790, and supplies it to the I/O chip 770 via the RAM 720. The I/O chip 770 couples the flexible disc 790 and various kinds of I/O devices via, for example, a parallel port, a serial port, a keyboard port and a mouse port.

The program to be provided to the analysis apparatus 40 is stored in various kinds of recording media such as the flexible disc 790, the CD-ROM 795 and an IC, and provided by the user thereto. The program is read out from the recording medium via the I/O chip 770 and/or the I/O controller 784, and installed in the analysis apparatus 40 to be executed.

The program which is installed in the analysis apparatus 40 to be executed includes an estimation input module, a unit distance transition probability supply module, a state transition probability supply module, an expression amount input module, and a state detection module. Furthermore, this program may use the hard disc drive 740 as the probability distribution storage unit 400 or the gene database 435. Since operations which the modules work on the analysis apparatus 40 to allow the analysis apparatus 40 to execute are the same as those of corresponding portions in the analysis apparatus 40 as described in FIGS. 1 to 6, descriptions for them are omitted.

The above described program and modules may be stored in an external recording medium. As the recording medium, an optical recording medium such as DVDs and PDs, a magneto-optical recording medium such as MDS, a tape medium, and a semiconductor memory such as IC cards can be used in addition to the flexible disc 790, the CD-ROM 795 and the like. A storage device such as hard discs and RAM provided in a server system coupled to a private communication network and Internet may be used as the recording medium, and the program may be provided to the analysis device 40 via the network.

As described in this embodiment, the analysis apparatus 40 can analyze the state of the chromosome 20 based on the results obtained by directly measuring the actual work of the gene by the expression microarray and the like. Thus, effective analysis can be realized based on information as to actions which the gene exerts on an organism in comparison with a method of directly observing the chromosome 20.

Furthermore, the analysis apparatus 40 can detect the combination of the chromosomal states maximizing the probability among those that the plurality of genes on the chromosome 20 assume, based on the measurement values of the expression amount measured for the genes arrayed on the chromosome 20. Thus, the analysis apparatus 40 judges the states of the chromosome 20 more precisely so that the analysis apparatus 40 can detect a region as the abnormal region, which has been buried in noises to be incapable of being detected.

Still furthermore, the analysis apparatus 40 can accomplish these processings by spending times in proportion to the number of genes and by use of the memories of an amount in proportion to the number of the genes. Thus, even when the number of the genes is enormous, an increase in the calculation time can be suppressed.

According to the embodiment described above, the analysis apparatus, the analysis method, the program and the recording medium, which are defined in the following items, are realized.

(Item 1) An analysis apparatus which analyzes chromosomal states based on amounts of expression of genes, the analysis apparatus comprising: a probability distribution storage unit for storing a probability distribution of amounts of expression of genes for each of a plurality of chromosomal states, when each gene, which is arrayed on the chromosome, assuming one of the chromosomal states whose distributions of amount of expression are different from others; a state transition probability supply unit for supplying a state transition probability indicating a probability in which, with regard to each gene arrayed on the chromosome, when one gene arrayed on the chromosome assumes any one of the chromosomal states, a certain gene arrayed next to the gene assumes any one of the chromosomal states; an expression amount input unit for receiving an expression amount measurement value that is a measurement value of the amount of expression for each gene on the chromosome; and a state detection unit for detecting, from combinations of chromosomal states that the plurality of genes on the chromosome assume, a combination that maximizes a probability that the amount of expression of the plurality of genes come to be the expression amount measurement value, based on the probability distribution and the state transition probability.

(Item 2) The analysis apparatus according to item 1, wherein the state transition probability supply unit acquires a distance between a gene and the gene next thereto with regard to each gene on the chromosome, and, when the distance is shorter, generates the state transition probability increasing a probability that the chromosomal states of the gene and the gene next thereto are equal, compared to those when the distance is longer.

(Item 3) The analysis apparatus according to item 2, the apparatus further comprising: a unit distance transition probability supply unit for supplying a unit distance transition probability that is a state transition probability between two genes arrayed adjacent to each other on the chromosome with a previously determined unit distance therebetween, and wherein the state transition probability supply unit generates the state transition probability between the two genes by raising the unit distance transition probability to the power of the number of times according to the distance between the genes adjacent to each other on the chromosome.

(Item 4) The analysis apparatus according to item 3, wherein the probability distribution storage unit stores the probability distribution of the amount of expression of the gene when the gene assumes any one of the deletion, amplification and normal states; the state transition probability supply unit supplies, for any one of the deletion, amplification, and normal states to be assumed by the gene, a probability of any one of the deletion, amplification, and normal states to be assumed by a gene adjacent to the gene arrayed on the chromosome as a state transition probability. the state detection unit, among all the combinations of any one of the deletion, amplification, and normal states to be assumed by the gene with any one of the deletion, amplification, and normal states to be assumed by the adjacent gene, detects a combination to maximize a probability that the amount of expression of the plurality of genes comes to be equal to the expression amount measurement value; and wherein the chromosomal state of each gene is any one of a deletion state, an amplification state and a normal state, the deletion state indicating that the gene is in a deletion region of the chromosome, the amplification state indicating that the gene is in an amplification region thereof, and the normal state indicating that the gene is in a normal region thereof;

(Item 5) The analysis apparatus according to item 4, the apparatus further comprising: an estimation value input unit for receiving an estimation value of a deletion distance that is a length of the deletion region continuous in the chromosome and an estimation value of an amplification distance that is a length of the amplification region continuous therein, and when the chromosome is sequentially observed from an end thereof, the unit distance transition probability supply unit generates a probability that a position that is by the unit distance away from a position that is the deletion region comes to be the normal region, by multiplying the unit distance with an inverse number of the deletion distance inputted from the estimation value input unit, and generates a probability that a position that is by the unit distance away from a position that is the amplification region comes to be the normal region, by multiplying the unit distance with an inverse number of the amplification distance inputted from the estimation value input unit.

(Item 6) The analysis apparatus according to item 5, wherein the estimation value input unit receives an estimation value of a region ratio that is a ratio of the deletion, amplification and normal regions; the unit distance transition probability supply unit generates zero as two probabilities, among the unit distance transition probabilities, that one of the positions that are by the unit distance away on the chromosome is the deletion region and the other position is the amplification region, and generates the other unit distance transition probabilities based on the region ratio inputted from the estimation value input unit.

(Item 7) The analysis apparatus according to item 4, wherein, based on a vector indicating a probability of any one of the deletion, amplification, and normal regions representing the predetermined position on the chromosome, the unit distance transition supply unit supplies a matrix Q as the unit distance transition probability for calculating a vector indicating respective probabilities of the deletion, amplification, and normal regions representing the position that is by the unit distance away from the predetermined position; and the state transition probability supply unit generates, as Q (L) that is the state transition probability between two adjacent genes distant from each other by a distance L times the unit distance, a product of an inverse matrix of a matrix W in which each of eigenvectors of the matrix Q is arranged in a row direction, a matrix Λ to the power of L in which each of eigenvalues of the matrix Q is arranged in a diagonal element, and the matrix W, noting that the matrix Q is expressed by an equation (1) wherein, when the chromosome is sequentially observed from an end thereof, an $\alpha$ is set for a probability that a position that is by the unit distance away from a position that is the deletion region comes to be the normal region, a $\beta_1$ is set for a probability that a position that is by the unit distance away from a position that is the normal region comes to be the deletion region, a $\beta_2$ is set for a probability that a position that is by the unit distance away from a position that is the normal region comes to be the amplification region, and a $\gamma$ is set for a probability that a position that is by the unit distance away from a position that is the amplification region comes to be the normal region $$Q = \{q_{ij}\} = \begin{pmatrix} 1-\alpha & \alpha & 0 \\ \beta_1 & 1-\beta_1-\beta_2 & \beta_2 \\ 0 & \gamma & 1-\gamma \end{pmatrix} \quad (21)$$

wherein the matrixes W and Λ to the power of L are expressed by the equation (22), noting that the eigenvectors of the matrix Q shall be $w_1$, $w_2$ and $w_3$, and the eigenvalues corresponding to these eigenvectors shall be 1, $\lambda_2$, and $\lambda_3$, $$W = \begin{pmatrix} w_1 \\ w_2 \\ w_3 \end{pmatrix} \text{ and } \Lambda^L \begin{pmatrix} 1 & 0 & 0 \\ 0 & \lambda_2^L & 0 \\ 0 & 0 & \lambda_3^L \end{pmatrix} \quad (22)$$

and wherein
the matrix Q(L) is expressed by the following equation (23).

$$Q(L) = \{q_{ij}(L)\} = Q^L = W^{-1}\Lambda^L W \quad (23)$$

(Item 8) The analysis apparatus according to Item 4, wherein, based on a detected combination of chromosomal states, the state detection unit detects and displays, as an abnormal region on the chromosome, a portion in which the distance between adjacent genes is equal to, or shorter than, a prescribed length, among portions in which genes in the amplification state appear one after another and portions in which genes in the deletion state appear one after another.

(Item 9) The analysis apparatus according to Item 1, wherein, using a Hidden Markov Model in which the plurality of chromosomal states are grouped into sets of hidden states, in which the amounts of gene expression of the plurality of genes represented by the measured amounts of gene expression are set as outputted sequences, and in which the probability distributions are set respectively as the output probabilities of the chromosomal states, the state detection unit calculate a state transition sequence that maximizes a state transition probability in the Hidden Markov Model, and accordingly detects a combination of chromosomal states of adjacent genes that maximizes the probability that the amount of gene expression of each of the plurality of genes are equal to the measured amounts of expression of the gene.

(Item 10) An analysis method for analyzing the state of a chromosome based on amounts of expression of genes, given that each of the plurality of genes arrayed on the chromosome takes on one of the plurality of chromosomal states whose distributions of amounts of gene expression differ from one another, and given that the probability distribution of the amount of gene expression of a gene is determined for the chromosomal state of the gene; and comprising of steps of: supplying, with regard to each gene and the chromosomal state thereof on the chromosome, the state transition probabilities represented by the probability of a gene in one of the plurality of chromosomal states having a gene, arrayed adjacent to the gene on the chromosome, whose chromosomal state is one of the plurality of chromosomal states, by the probability of the gene in the chromosomal state in having the adjacent gene whose chromosomal state is another of the plurality of chromosomal states, and by the probability of the gene in the chromosomal state having the adjacent gene whose chromosomal state is the other of the plurality of chromosomal states; receiving the amount of gene expression that is the measured amount of gene expression for each gene on the chromosome; and detecting, based on the probability distributions and the state transition probabilities, among combinations of chromosomal states that a plurality of genes on the chromosome can create, a combination that maximizes the probability that each of the amounts of gene expression of the plurality of genes is equal to the expression amount measurement value of the gene.

(Item 11) A program which is a program to cause a computer to function as an analysis apparatus for analyzing chromosomal states based on amounts of gene expression of genes, and which, given that each of the plurality of genes arrayed on the chromosome takes on one of the plurality of chromosomal states whose distributions of amounts of gene expression differ from one another, causes a computer to function as: a probability distribution storage unit for storing the probability distribution of the amount of expression for each gene; a state transition probability supply unit for supplying, with regard to each gene and the chromosomal state thereof on the chromosome, the state transition probabilities represented by the probability of a gene in one of the plurality of chromosomal states having an gene, arrayed adjacent to the gene on the chromosome, whose chromosomal state is one of the plurality of chromosomal states, by the probability of the gene in the chromosomal state in relation to the adjacent gene whose chromosomal state is another of the plurality of chromosomal states, and by the probability of the gene in the chromosomal state in relation to the adjacent gene whose chromosomal state is the other of the plurality of chromosomal states; an expression amount input unit for receiving the amount of gene expression that is the measured amount of gene expression for each gene on the chromosome; and a state detection unit for detecting, based on the probability distributions and the state transition probabilities, among combinations of chromosomal states that a plurality of genes on the chromosome can create, a combination that maximizes the probability that each of the amounts of gene expression of the plurality of gene is equal to the expression amount measurement value of the gene.

(Item 12) A recording medium in which the program according to item 11 is recorded.

While the present invention has been described by way of the preferred embodiment, it is to be understood that the scope and spirit of the appended claims are not limited to the disclosed embodiment. Various modification and changes of the disclosed embodiment will be become apparent to persons skilled in the art. It is apparent from the description of the appended claims that the embodiment modified is within the scope and spirit of the present invention. Thus, according to the present invention, chromosomes can be analyzed with a high precision and at a high speed.

Although the preferred embodiment of the present invention has been described in detail, it should be understood that various changes, substitutions and alternations can be made therein without departing from spirit and scope of the inventions as defined by the appended claims. Variations described for the present invention can be realized in any combination desirable for each particular application. Thus particular limitations, and/or embodiment enhancements described herein, which may have particular advantages to a particular application need not be used for all applications. Also, not all limitations need be implemented in methods, systems and/or apparatus including one or more concepts of the present invention.

The present invention can be realized in hardware, software, or a combination of hardware and software. A visualization tool according to the present invention can be realized in a centralized fashion in one computer system or in a distributed fashion where different elements are spread across several interconnected computer systems. Any kind of computer system—or other apparatus adapted for carrying out the methods and/or functions described herein—is suitable. A typical combination of hardware and software could be a general purpose computer system with a computer program that, when being loaded and executed, controls the computer system such that it carries out the methods described herein. The present invention can also be embedded in a computer program product, which comprises all the features enabling the implementation of the methods described herein, and which—when loaded in a computer system—is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form.

Thus the invention includes an article of manufacture which comprises a computer usable medium having computer readable program code means embodied therein for causing a function described above. The computer readable program code means in the article of manufacture comprises computer readable program code means for causing a computer to effect the steps of a method of this invention. Similarly, the present invention may be implemented as a computer program product comprising a computer usable medium having computer readable program code means embodied therein for causing a function described above. The computer readable program code means in the computer program product comprising computer readable program code means for causing a computer to affect one or more functions of this invention. Furthermore, the present invention may be implemented as a program storage device readable by machine, tangibly embodying a program of instructions executable by the machine to perform method steps for causing one or more functions of this invention.

It is noted that the foregoing has outlined some of the more pertinent objects and embodiments of the present invention. This invention may be used for many applications. Thus, although the description is made for particular arrangements and methods, the intent and concept of the invention is suitable and applicable to other arrangements and applications. It will be clear to those skilled in the art that modifications to the disclosed embodiments can be effected without departing from the spirit and scope of the invention. The described embodiments ought to be construed to be merely illustrative of some of the more prominent features and applications of the invention. Other beneficial results can be realized by applying the disclosed invention in a different manner or modifying the invention in ways known to those familiar with the art.

What is claimed is:

1. A system for analyzing the state of a chromosome based on amounts of gene expression, the system comprising one or more processors and a non-transitory computer-readable storage medium encoded with a plurality of computer-executable programs, wherein execution of the programs by the one or more processors causes the system to perform functions of:
analyzing a gene expression measurement for each of the plurality of genes;
determining a probability distribution ($b_i$) of an amount of gene expression ($e_k$) for each of a plurality of genes $g_k$ (k=1, 2, . . . , N) sequentially arrayed on the chromosome, wherein the probability distribution is determined by the equation:

$$b_i(e_k) = \frac{1}{\sqrt{2\Pi}\sigma_i} \exp\left(-\frac{(e_k - \mu_i)^2}{2\sigma_i^2}\right) \times \Delta e,$$

wherein the gene expression of at least one of the plurality of chromosomal states is different than the gene expression of another of the plurality of chromosomal states;

generating a state transition probability for each of the plurality of genes, wherein the state transition probability indicates a probability that a gene will assume a chromosomal state equal to a chromosomal state of an adjacent gene, wherein the chromosomal state comprises one of a deletion state, an amplification state, and a normal state, the deletion state indicating that the gene is in a deletion region of the chromosome, the amplification state indicating that the gene is in an amplification region thereof, and the normal state indicating that the gene is in a normal region thereof; and detecting the chromosomal state of each of the plurality of genes by: (i) calculating a combination of chromosomal states for the plurality of genes on the chromosome based on the probability distribution obtained via the probability distribution storage unit and the state transition probability, wherein calculating a combination of chromosomal states for the plurality of genes on the chromosome comprises sequentially calculating a probability value δ for each of the plurality of genes and chromosomal states on the chromosome via $$\delta_k(j) = \max_i |\delta_{k-1}(i) q_{ij}(l_k)| b_j(e_k),$$

wherein k represents position on the chromosome and i represents one of the three chromosomal states, and wherein $q_{ij}$ represents a unit distance transition probability for calculating a vector indicating respective transition probabilities of a position which is a unit distance away from a deletion, amplification, or normal region; and (ii) determining the combination of genes and chromosomal states with the highest probabilities of deletion and/or amplification regions associated with an abnormal region on the chromosome that is indicative of increased disease progression, and outputting at least one abnormal region to a user in a user readable format.

2. The system of claim 1, wherein the state transition probability supply unit acquires a distance between the gene and the adjacent gene, wherein the probability of the gene assuming a chromosomal state equal to the chromosomal state of the adjacent gene is higher when the distance is shorter and lower when the distance is longer.

3. The system of claim 2, wherein execution of the programs by the one or more processors causes the system to perform a function of calculating a unit distance transition probability that is a state transition probability between two genes arrayed adjacent to each other on the chromosome based on a previously determined unit distance therebetween.

4. The system of claim 3, execution of the programs by the one or more processors causes the system to perform functions of:

storing the probability distribution of gene expression of a gene when the gene assumes any one of the deletion, amplification, and normal states;

supplying a state transition probability to a gene, a state transition probability of an adjacent gene assuming any one of the deletion, amplification, and normal states; and detecting a state combination for the plurality of genes with the highest probability to produce the gene expression measurement.

5. The system of claim 4, wherein execution of the programs by the one or more processors causes the system to perform a function of receiving at least one of an estimated length of a deletion region on the chromosome and an estimated length of an amplification region on the chromosome; and wherein the unit distance transition probability supply unit is further operative to at least one of: (i) generate a probability that a position on the chromosome, which is a previously-determined unit distance away from a deletion region, is a normal region, wherein the probability is generated by multiplying the unit distance with the inverse of the received estimated length of a deletion region; and (ii) generate a probability that a position on the chromosome, which is a previously-determined unit distance away from an amplification region, is a normal region, wherein the probability is generated by multiplying the unit distance with the inverse of the received estimated length of an amplification region.

6. The system of claim 5, wherein the estimation value input unit receives an estimated region ratio that expresses a ratio of the deletion, amplification, and normal regions of the chromosome.

7. The system of claim 4, wherein execution of the programs by the one or more processors causes the system to perform a function of the unit distance transition supply unit: (i) supplying a matrix Q as the unit distance transition probability for calculating a vector indicating respective transition probabilities of a position which is a unit distance away from a deletion, amplification, or normal region; and (ii) generating, as Q(L), the state transition probability between two adjacent genes distant from each other by a distance L times the unit distance, a product of an inverse matrix of a matrix W in which each of eigenvectors of the matrix Q is arranged in a row direction, a matrix κ to the power of L in which each of eigenvalues of the matrix Q is arranged in a diagonal element, and the matrix W, wherein the matrix Q is expressed by an equation (1), wherein an α is set for a probability that a position that is by the unit distance away from a position that is the deletion region comes to be the normal region, a $\beta_1$ is set for a probability that a position that is by the unit distance away from a position that is the normal region comes to be the deletion region, a $\beta_2$ is set for a probability that a position that is by the unit distance away from a position that is the normal region comes to be the amplification region, and a γ is set for a probability that a position that is by the unit distance away from a position that is the amplification region comes to be the normal region $$Q = \{q_{ij}\} = \begin{pmatrix} 1-\alpha & \alpha & 0 \\ \beta_1 & 1-\beta_1-\beta_2 & \beta_2 \\ 0 & \gamma & 1-\gamma \end{pmatrix} \quad (1)$$

wherein the matrixes W and Λ to the power of L are expressed by the equation (2), wherein the eigenvectors of the matrix Q shall be $w_1$, $w_2$ and $w_3$, and the eigenvalues corresponding to these eigenvectors shall be 1, $\lambda_2$, and $\lambda_3$, $$W = \begin{pmatrix} w_1 \\ w_2 \\ w_3 \end{pmatrix} \text{ and } \Lambda^L = \begin{pmatrix} 1 & 0 & 0 \\ 0 & \lambda_2^L & 0 \\ 0 & 0 & \lambda_3^L \end{pmatrix} \quad (2)$$

and wherein
the matrix Q(L) is expressed by the following equation (3)

$$Q(L) = \{q_{ij}(L)\} = Q^L = W^{-1} \Lambda^L W \quad (3).$$

8. The system of claim 4, wherein the state detection unit detects and displays an abnormal region of the chromosome, wherein a distance between each of the plurality of genes in the abnormal region is equal to, or shorter than, a prescribed length, further wherein the genes in an amplification state appear one after another and the genes in a deletion state appear one after another.

9. The system of claim 1, wherein the state detection unit: (i) uses a Hidden Markov Model in which the plurality of chromosomal states are grouped into sets of hidden states, in which the received gene expression measurements for each of the plurality of genes are set as observed output, and in which the probability distributions are set respectively as the output probabilities of the chromosomal states; (ii) calculates a state transition sequence that maximizes a state transition probability in the Hidden Markov Model; and (iii) detects a combination of chromosomal states of adjacent genes that maximizes the probability that the gene expression of each of the plurality of genes is equal to the gene expression measurements.

10. An analysis method for determining a chromosomal state of a plurality of genes on a chromosome based on gene expression, wherein the method is run on a system comprising one or more distinct programs, each of the one or more distinct programs being embodied on a tangible computer-readable recordable storage medium, the method comprising:

analyzing a gene expression measurement for each of the plurality of genes, wherein receiving a gene expression measurement for each of the plurality of genes is carried out by an expression amount input program executing on a hardware processor;

determining a probability distribution ($b_i$) of an amount of gene expression ($e_k$) for each of a plurality of genes $g_k$ (k=1, 2, ..., N) sequentially arrayed on the chromosome, wherein the probability distribution is determined by the equation:

$$b_i(e_k) = \frac{1}{\sqrt{2\Pi}\,\sigma_i} \exp\left(-\frac{(e_k - \mu_i)^2}{2\sigma_i^2}\right) \times \Delta e,$$

wherein the gene expression of at least one of the plurality of chromosomal states is different than the gene expression of another of the plurality of chromosomal states, wherein obtaining a probability distribution for each of a plurality of genes arrayed on the chromosome is carried out by a probability distribution storage program executing on a hardware processor;

generating a state transition probability for each of the plurality of genes, wherein the state transition probability indicates a probability that a gene will assume a chromosomal state equal to a chromosomal state of an adjacent gene, wherein the chromosomal state comprises one of a deletion state, an amplification state, and a normal state, the deletion state indicating that the gene is in a deletion region of the chromosome, the amplification state indicating that the gene is in an amplification region thereof, and the normal state indicating that the gene is in a normal region thereof, and wherein generating a state transition probability for each of the plurality of genes is carried out by a state transition probability supply program executing on a hardware processor;

detecting the chromosomal state of each of the plurality of genes by: (i) calculating a combination of chromosomal states for the plurality of genes on the chromosome based on the probability distribution obtained via the probability distribution storage program and the state transition probability generated via the state transition probability supply program, wherein calculating a combination of chromosomal states for the plurality of genes on the chromosome comprises sequentially calculating a probability value δ for each of the plurality of genes and chromosomal states on the chromosome via $$\delta_k(j) = \max_i |\delta_{k-1}(i) q_{ij}(l_k)| b_j(e_k),$$

wherein k represents position on the chromosome and i represents one of the three chromosomal states, and wherein $q_{ij}$ represents a unit distance transition probability for calculating a vector indicating respective transition probabilities of a position which is a unit distance away from a deletion, amplification, or normal region; and (ii) determining the combination of genes and chromosomal states with the highest probabilities of deletion and/or amplification regions associated with an abnormal region on the chromosome that is indicative of increased disease progression, wherein detecting the chromosomal state of the plurality of genes is carried out by a state detection program executing on a hardware processor; and outputting the at least one abnormal region to a user in a user readable format.

* * * * *